US006867306B2

(12) United States Patent
Srinath et al.

(10) Patent No.: US 6,867,306 B2
(45) Date of Patent: Mar. 15, 2005

(54) PROCESS FOR THE SYNTHESIS OF ATORVASTATIN FORM V AND PHENYLBORONATES AS INTERMEDIATE COMPOUNDS

(75) Inventors: Sumitra Srinath, Karnataka (IN); Joy Mathew, Karnataka (IN); Sandhya Ujire, Karnataka (IN); Madhavan Sridharan, Karnataka (IN); Ganesh Sambasivam, Karnataka (IN)

(73) Assignee: Biocon Limited, Karnataka (IN)

( * ) Notice: Subject to any disclaimer, the term of this patent is extended or adjusted under 35 U.S.C. 154(b) by 0 days.

(21) Appl. No.: 10/466,802

(22) PCT Filed: Jun. 14, 2001

(86) PCT No.: PCT/IN01/00114

§ 371 (c)(1),
(2), (4) Date: Jul. 16, 2003

(87) PCT Pub. No.: WO02/057274

PCT Pub. Date: Jul. 25, 2002

(65) Prior Publication Data

US 2004/0072893 A1 Apr. 15, 2004

(30) Foreign Application Priority Data

Jan. 19, 2001 (WO) ............................... PCT/IN01/00006

(51) Int. Cl.$^7$ .......................... C07D 405/02; C07F 5/02
(52) U.S. Cl. ........................ 548/517; 548/530; 558/288
(58) Field of Search ................................ 548/517, 530; 558/288

(56) References Cited

U.S. PATENT DOCUMENTS

| 4,681,893 A | 7/1987 | Roth ........................... 514/422 |
| 5,003,080 A | 3/1991 | Butler et al. ................. 548/517 |
| 5,084,392 A | 1/1992 | Miyazawa et al. .......... 435/280 |
| 5,097,045 A | 3/1992 | Butler et al. ................. 549/373 |
| 5,103,024 A | 4/1992 | Millar et al. ................. 549/373 |
| 5,124,482 A | 6/1992 | Butler et al. ................. 564/169 |
| 5,149,837 A | 9/1992 | Butler et al. ................. 549/333 |
| 5,155,251 A | 10/1992 | Butler et al. ................. 558/442 |
| 5,216,174 A | 6/1993 | Butler et al. ................. 548/517 |
| 5,245,047 A | 9/1993 | Butler et al. ................. 548/517 |
| 5,248,793 A | 9/1993 | Millar et al. ................. 549/375 |
| 5,273,995 A | 12/1993 | Roth ........................... 514/422 |
| 5,292,939 A | 3/1994 | Hollingsworth ............. 562/515 |
| 5,319,110 A | 6/1994 | Hollingsworth ............. 549/313 |
| 5,374,773 A | 12/1994 | Hollingsworth ............. 562/515 |
| 5,397,792 A | 3/1995 | Butler et al. ................. 514/326 |
| 6,274,740 B1 | 8/2001 | Lin et al. |
| 6,528,661 B2 | 3/2003 | Niddam et al. |
| 2002/0099224 A1 | 7/2002 | Niddam et al. |
| 2003/0114685 A1 | 6/2003 | Niddam-Hildesheim et al. |
| 2003/0175338 A1 | 9/2003 | Singh et al. |

FOREIGN PATENT DOCUMENTS

| WO | WO 97/03958 | 2/1997 |
| WO | WO 97/03960 | 2/1997 |
| WO | WO 00/53566 | 9/2000 |
| WO | WO 00/68221 | 11/2000 |
| WO | WO 01/10813 | 2/2001 |
| WO | WO 01/28999 | 4/2001 |
| WO | WO 01/42209 | 6/2001 |
| WO | WO 01/72706 | 10/2001 |
| WO | WO 02/43667 A2 | 6/2002 |
| WO | WO 02/057228 | 7/2002 |
| WO | WO 03/004450 A1 | 1/2003 |
| WO | WO 03/004455 A2 | 1/2003 |
| WO | WO 03/004456 | 1/2003 |
| WO | WO 03/016317 | 2/2003 |

OTHER PUBLICATIONS

International Search Report issued for corresponding PCT application PCT/IN01/00114 (WO02/027274 A1).

Akira et al., "A Novel Synthesis of (R)– and (S)–4–Hydroxytetrahydrofuran–2–ones", *Synthesis*, 6:570–573, 1987.

Baumann, et al., "The Convergent Synthesis of CI–981, an Optically Active, Highly Potent, Tissue Selective Inhibitor of HMG–CoA Reductase", *Tetrahedron Letters*, 33(17):2283–2284 (1992).

Saito, et al., "Combination of Borane–Dimethyl Sulfide Complex with Catalytic Sodium Tetrahydroborate as a Selective Reducing Agent for α–Hydroxy Esters, Versatile Chiral Building Block from (S)–(–)–Malic Acid,", *Chemistry Letters*, 1389–1392 (1984).

Shieh et al., "Stereoselective Alkylation and Aldol Reactions of (S)–(–)–β–Hydroxy–γ–butyrolactone Dianion", *J. Org. Chem.*, 46:4319–4321 (1981).

Graul et al., "Atorvastatin calcium", Drugs of the future (1997), 22(9), 956–968.

Lee et al., "Atorvastatin, an HMG–CoA reductase inhibitor and effective lipid–regulating agent. Part II. Synthesis of side chain–labeled [14C] atorvastatin", Journal of Labeled Compounds Radiopharmaceuticals (1999), 42(2), 129–133.

Manzoni et al., "Biosynthesis and biotechnological production of statins by filamentous fungi and application of these cholesterol–lowering drugs", Applied Microbiology and Biotechnology (2002), 58(5), 555–564.

Oehrlein R et al., "Chemoenzymatic approach to statin side–chain building blocks" Advanced Synthesis Catalysis (2003), 345 (6+7), 713–715.

(List continued on next page.)

Primary Examiner—Kamal Saeed
(74) Attorney, Agent, or Firm—Sam Pasternack; Nadege Lagneau; Choate, Hall & Stewart

(57) ABSTRACT

The present invention discusses a novel process for the synthesis of [R-(R*,R*)]-2-(4-fluorophenyl)-B,D-dihydroxy-5-(1-methylethyl)-3-phenyl-4-[(phenylamino) carbonyl]-1H-pyrrole-1-heptanoic acid hemi calcium, atorvastatin. The compound so prepared is useful as inhibitor of the HMG-CoA reductase and may thus be used as hypolipidemic and hypocholesterolemic agent.

7 Claims, No Drawings

OTHER PUBLICATIONS

Radl et al., "An Improved synthesis of 1,1–dimethylethyl–6–cyanomethyl–2,2–dimethyl–1, 3–dioxane–4–acetate, a key intermediate for atorvastatin synthesis", Tetrahedron Letters (2002), 43(11), 2087–2090.

Roth, Bruce D., "The discovery and development of atorvastatin, a potent novel hypolipidemic agent", Progress in Medicinal Chemistry (2002), 40, 1–22.

Wierzbicki, Anthony S., "Atorvastatin", Expert Opinion on Pharmacotherapy (2001), 2(5), 819–830.

Woo et al., "Atorvastatin, an HMG–CoA reductase inhibitor and effective lipid–regulating agent. Part I. Synthesis of ring–labeled [14C] atorvastatin", Journal of Labeled Compounds Radiopharmaceuticals (1999), 42(2), 121–127.

Woo et al., "Atorvastatin, an HMG–CoA reductase inhibitor and effective lipid–regulating agent. Part III. Synthesis of [2H5]–, [13C8], and [13C7, 15N] atorvastatin and their application in metabolic and pharmacokinetic studies", Journal of Labeled Compounds Radiopharmaceuticals (1999), 42(2), 135–145.

PROCESS FOR THE SYNTHESIS OF ATORVASTATIN FORM V AND PHENYLBORONATES AS INTERMEDIATE COMPOUNDS

PRIORITY CLAIM

The present application claims the benefit under 35 U.S.C. § 371 of International Application No.: PCT/IN01/00114 (published PCT application No. WO 02/057274), filed 14 Jun. 2001, which claims priority to International Application No.: PCT/IN01/00006 (published PCT application No. WO 02/057229), filed 19 Jan. 2001, the entire contents of each of these applications are hereby incorporated herein by reference.

FIELD OF THE INVENTION

This invention relates to a process for manufacturing R-(R*,R*)]-2-(4-fluorophenyl)-B,D-dihydroxy-5-(1-methylethyl)-3-phenyl-4-[(phenylamino)carbonyl]-1H-pyrrole-1-heptanoic acid hemi calcium salt, atorvastatin and novel intermediates produced during the course of manufacture. The said compound is useful as inhibitor of the enzyme HMG-CoA reductase and is thus useful as an hypolipidemic and hypocholesterolemic agent.

BACKGROUND OF THE INVENTION

U.S. Pat. No. 4,681,893, discloses a route using resolution of the racemic product using R (+) α-methyl benzyl amine. U.S. Pat. No. 5,003,080 discloses a synthetic route for the preparation of the chiral form of atorvastatin. The patent discloses a process for the preparation of the lactone or its salts by coupling an ester of (4R)-6-(2-aminoethyl)-2,2-dialkyl-1,3-dioxane-3-acetate with 4-fluoro-α-[2-methyl-1-oxopropyl]γ-oxo-N-β-diphenylbenzenebutaneamide followed by deprotection and hydrolysis to give the product. The product suffers from the fact that ozonolysis is required as one of the steps for the synthesis of the amino ketal intermediate, which is hazardous for large scale preparation. The patent describes an alternate procedure wherein 4-fluoro-α-[2-methyl-1-oxopropyl]γ-oxo-N-β-diphenylbenzenebutaneamide is reacted with 3-amino propinaldehyde acetal followed by conventional procedures to give atorvastatin.

U.S. Pat. No. 5,216,174, No. 5,097,045, No. 5,103,024, No. 5,124,482, No. 5,149,837, No. 5,155,251, No. 5,245,047, No. 5,273,995, No. 5,248,793, and. No. 5,397,792 describe various minor modifications in the procedure for the preparation of atorvastatin calcium salt.

Synthesis of esters of (4R)-6-(2-aminoethyl)-2,2-dialkyl-1,3-dioxane-3-acetate is an important part of the preparation of atorvastatin calcium. U.S. Pat. No. 5,155,251 also discloses a synthetic route for the synthesis of (3R)-4-cyano-3-hydroxy butyric acid esters from (S)-3-hydroxy butyrolactone, which in turn is synthesized from a suitable carbohydrate substrate.

Other patents like U.S. Pat. Nos. 5,292,939, 5,319,110 and 5,374,773 disclose the preparation of 3,4-dihydroxybutyric acid. However, isolation of this highly water soluble compound or its lactone is not attempted.

Another multi step procedure starting from (S)-malic acid (J. org. Chem., 1981, 46, 4319) is reported. Esters of (S)-malic acid have also been used (Chem. Lett., 1984, 1389) for the synthesis of the hydroxy lactone involving BMS-NaBH4 reduction, followed by lactonization. While a six step procedure from D-isoascorbic acid is also reported (Syn., 1987, 570) but this process requires a silica gel chromatographic separation of the diastereomeric mixtures.

Optical resolution of the racemic hydroxylactones using lipase is disclosed in U.S. Pat. No. 5,084,392 but this method suffers from poor enantiomeric excess and loss of the other active isomer.

Thus, the above procedures involve cumbersome reaction conditions or expensive starting materials, reagents which are difficult to handle or hazardous for scale up, coupled with a multi step procedure which results in poor overall yield.

One object of the present invention is to disclose an inexpensive, simple and scalable route for the synthesis of atorvastatin. PCT pending application filed on Mar. 28, 2000 (PCT/IN00/00030) discloses a process for the synthesis but uses a different amino acid fragment for the condensation reaction to get atorvastatin calcium.

DETAILED DESCRIPTION OF CERTAIN PREFERRED EMBODIMENTS OF THE INVENTION

The process of the present invention in its first aspect is a new, improved, economical, and commercially feasible method for preparing HMG CoA reductase inhibitors of Formula XII which are useful as inhibitors of the enzyme HMG CoA reductase and are thus useful as hypolipidemic or hypocholesterolemic agents; an embodiment of which is outlined in Schemes 1–4.

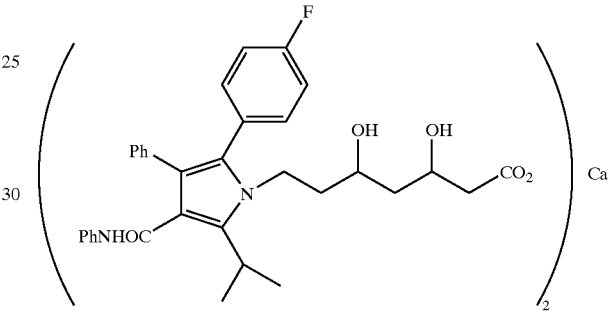

XII

Accordingly, the present invention provides a process for the synthesis of Atorvastatin (formula XII, said process comprising steps of:

a) reacting a compound of formula X with a compound of structure IV in a mixture of solvents selected from xylene, cyclohexane, methyl tert-butyl ether, diisopropyl ether, and acetonitrile, in the presence of a catalyst selected from pivalic acid, trifluromethyl sulfonic acid, methane sulfonic acid and p-toluene sulfonic acid, to give an intermediate of structure XI, and b) hydrolysis of the compound of structure XI followed by calcium salt formation to get the compound of formula XII.

The compound of Formula X used in step (a) where R is selected from $C_6H_5$ or substituted phenyls is prepared by:

a) reacting a compound of formula V with dihydro pyran to give a protected ether of formula VI, b) reacting the compound of formula VI with tert-butyl acetate with a base at −30 to −80° C. to give a compound of formula VII, c) reducing the compound of formula VII with a reducing agent to give a compound of formula VIII, d) reacting the compound of formula VIII with a protecting group to form a protected boronate ester of formula IX, and e) reducing the compound of formula IX to give a compound of formula X.

The reducing agent used in step (c) is selected from zinc borohydride.

The protecting group used in step (d) is selected from phenyl boronic acid, tolyl boronic acid and 3-nitro benzene boronic acid.

An intermediate of formula IX, where R is selected from C₆H₅ or substituted phenyl.

An intermediate of formula X, where R is selected from C₆H₅ or substituted phenyl.

An intermediate of formula XI, where R is selected from C₆H₅ or substituted phenyl.

The synthetic scheme for the synthesis of the amino ester of formula X is outlined in scheme 1.

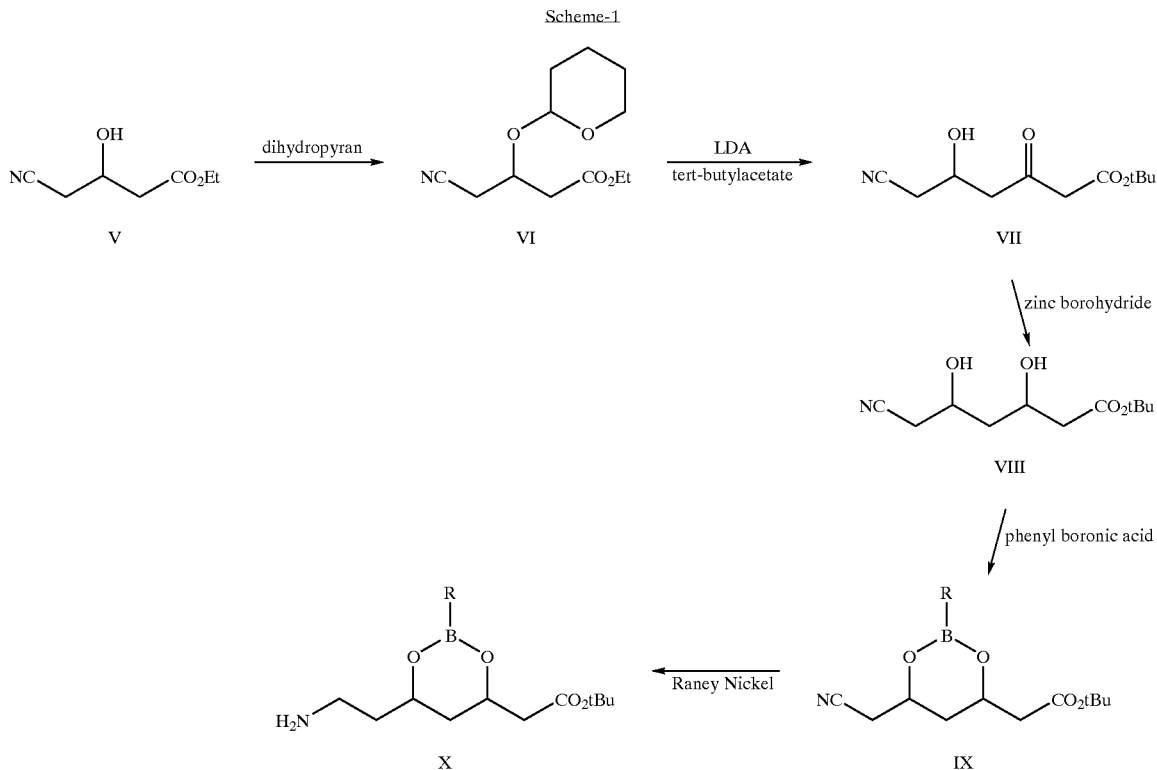

Thus, a cyano hydroxyester of formula V is treated with dihydropyran in the presence of p-toluenesulfonic acid in a solvent like, CH₂Cl₂, CH₃CN, DMF etc., to give the protected ether of formula VI, which is subsequently treated with the anion of tert-butyl acetate generated by reacting tert-butyl acetate with lithium diisopropylamide in THF to give a compound of formula A β-keto ester of formula XII is then reduced using zinc borohydride in THF to give a dihydroxy compound of formula VIII.

The dihydroxy ester compound of formula VIII is then protected using a boronic acid of formula RB(OH)₂; where R is chosen from phenyl or substituted phenyl to afford a boronate ester of Formula IX. Preferably, the reaction is carried out with phenyl boronic acid under a nitrogen atmosphere.

A boronate ester of Formula IX is then reduced using Raney Nickel to give the amino ester of formula X.

An amino ester of Formula X is reacted with a diketone of Formula IV wherein the process for the preparation of the compound of formula IV is described in scheme 2.

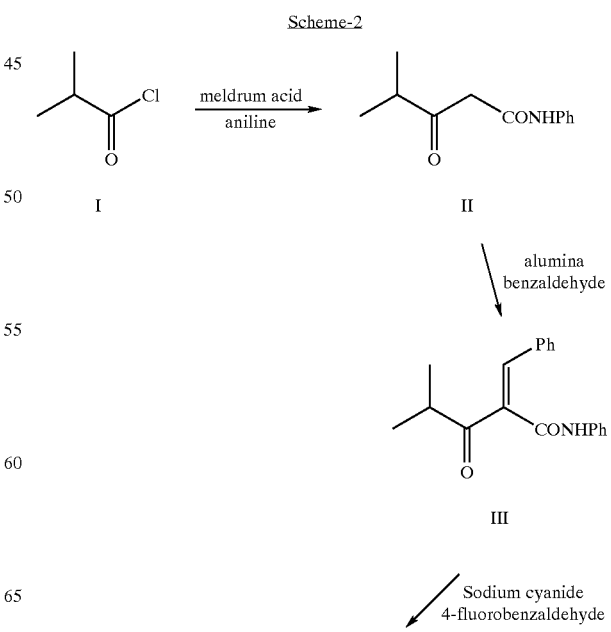

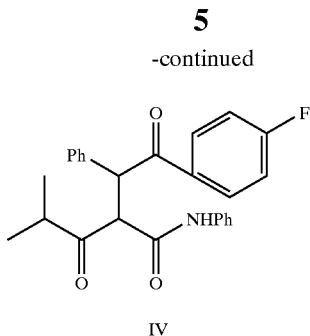

IV

A compound of formula IV is prepared as described in scheme 2, which comprises reacting isobutyryl chloride and meldrum's acid in the presence of a base chosen from pyridine, triethylamine, diisopropylethyl amine, dimnethylaniline etc. in CH$_2$Cl$_2$ at 0–5° C. for about 18h to give an acyl meldrum acid which is then reacted with aniline in a solvent chosen from CH$_2$Cl$_2$, acetonitrile, toluene etc., at the reflux temperature of the solvent for about 12h to afford the amide of formula II. Preferably the reaction is done in pyridine and CH$_2$Cl$_2$ at 0C. and in CH$_2$Cl$_2$ by stirring at room temperature.

The keto amide of formula II is then reacted with benzaldehyde in the presence of a base chosen from aqueous NaOH, or lithium hydroxide etc., and alumina for about 26h to give the methylenephenyl intermediate of formula III.

The compound of formula III is treated with 4-fluorobenzaldehyde in the presence of a catalyst chosen from metallic cyanide where the metal is Ag, K, Na, Cu, tetraalkylammonium etc., or trimethylsilyl cyanide in a polar solvent chosen from DMSO, DMF, acetonitrile etc., at the reflux temperature of the solvent to give a compound of formula IV. Preferably the reaction is carried out by reacting 4-fluorobenzaldehyde and sodium cyanide in DMSO at reflux temperature.

The diketone of formula IV is reacted with the amino ester of formula X as described in Scheme 3 in the presence of a catalyst of Formula R$_{12}$SO$_3$H, wherein R$_{12}$ is chosen from CF$_3$, CH$_3$, p-CH$_3$C$_6$H$_4$ and a solvent or mixtures thereof such as, for example, acetonitrile, xylene, diisopropyl ether cyclohexane, methyl tert-butyl ether and the like for about 24 to about 48 hours from 5 to 10C. to about the reflux temperature of the solvent with the removal of water to afford a compound of Formula XI. Preferably, the reaction is carried out in the presence of methanesulfonic acid and a mixture of xylene-hexane at reflux for about 48 hours with the removal of water.

Scheme-3

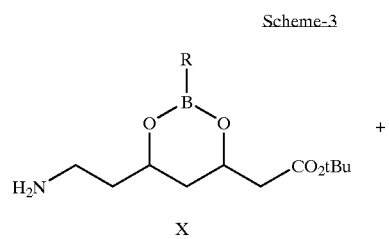

X

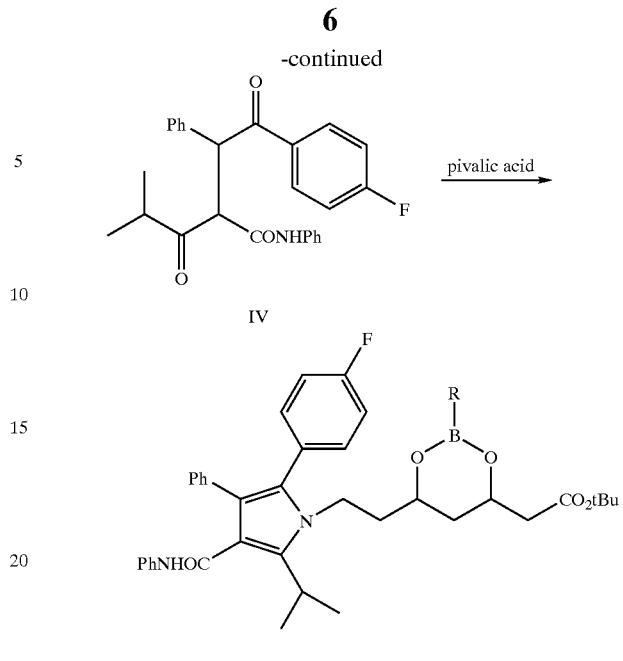

IV

XI

The compound of formula XI is converted to atorvastatin calcium as shown in scheme 4.

Scheme-4

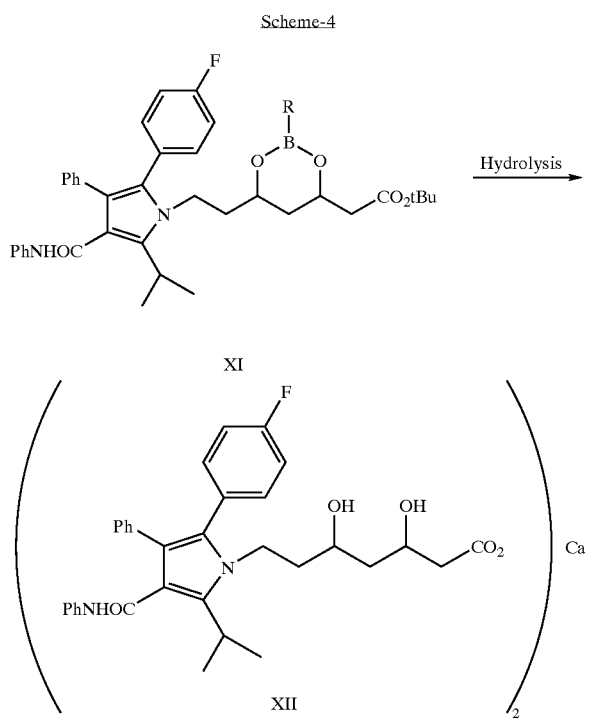

Scheme 4 involves the deprotection of the boronate ester followed by hydrolysis of the ester to give the free acid which is converted to its ammonium salt by reacting with either NH$_4$OH, methanolic NH$_3$ or by bubbling gaseous NH$_3$ to the solution of carboxylic acid in a solvent chosen from a mixture of EtOAc, hexane, diisopropyl ether, isopropanol, cyclohexane and methanol. Preferably the intermediate of formula XI is de-protected using aqueous sodium hydroxide at room temperature over a period of 24h and is then hydrolyzed using methanolic sodium hydroxide and acidified using diluted HCl to give the free acid which is converted to its ammonium salt by passing gaseous NH$_3$

EXAMPLE 1

1.1 Preparation of 4-methyl-3-oxo-N-phenylpetanamide (Formula II).

To a suspension of malonic acid (104 g) in, acetic anhydride (120 mL) at room temperature, Conc. $H_2SO_4$ (3 mL) was added. The mixture was cooled to 20° C. followed by the addition of acetone (8 mL) drop wise. The contents were stirred at room temperature (15 min) and kept at 0–5° C. overnight and filtered. The solid was washed with cold water and cold acetone and dried. The crude material was recrystallized from acetone-hexane mixture.

Meldrum's acid (59 g) was dissolved in $CH_2Cl_2$ (200 mL) and cooled to 0C. Pyridine (73 mL) was added drop wise over a period of 30 min and the mixture was stirred for an additional 10 min. Isobutyryl chloride (44 g) was added drop wise over a period of 30 min. and the mixture was stirred at 0° C. for 1 h followed by stirring at room temperature over night. The mixture was poured into 1.5N HCl containing crushed ice. The layers were separated and the aqueous layer was extracted with $CH_2Cl_2$ (2×100 mL). The combined extracts were washed with 1.5N HCl (2–100 mL) followed by saturated $NH_4Cl$ solution (2×100 mL) and dried over $Na_2SO_4$ and concentrated under reduced pressure to afford the crude acyl meldrum's acid which was used for the next step.

The crude acyl meldrum's acid (84 g) was taken in benzene (300 mL) and aniline (111 mL) was added. The mixture was refluxed for 4h. Cool the reaction mixture to room temperature and wash with 2N HCl (5×100 mL) and benzene was removed under reduced pressure to get formula II.

EXAMPLE 1.2
Preparation of 4-methyl-3-oxo-N-phenyl-2-(phenylmethylene) pentanamide (Formula III).

The crude amide was added to a slurry of alumina impregnated with lithium hydroxide in tetrahydrofuran. To this mixture at room temperature benzaldehyde was added. The contents were allowed to stir under reflux for 2h. The contents were filtered, tetrahydrofuran was removed under reduced pressure and the residue was extracted with $CH_2Cl_2$. The organic extracts were washed with bicarbonate, bisulfite solution, dried and concentrated under reduced pressure to afford the crude compound of formula III.

EXAMPLE 1.3
Preparation of 4-fluoro-α-[2-methyl-l-oxopropyl]γ-oxo-N-β-diphenylbenzene butane amide (Formula IV).

To 4-fluorobenzaldehyde in anhydrous DMF, sodium cyanide was added and the contents were refluxed for 4h. To this the intermediate from example 3 was added and the contents were stirred for an additional 18h. Usual work up affords the crude diketo compound of formula IV.

EXAMPLE 1.4
Preparation of 4-cyano-3-(O-tetrahydropyranyl) butyric acid ethyl ester (Formula VI).

A solution of 50 g of 4-cyano-3-hydroxybutyric acid ethyl ester in dichloromethane (1 L) and dihydropyran (53.57 g) and catalytic quantity of PPTS (15.9 g) was stirred at room temperature over a period of 24 h. Upon completion, the contents were washed with bicarbonate, dried and solvent was removed under reduced pressure to give the title compound.

EXAMPLE 1.5
Preparation of tert-butyl 6-cyano-5-hydroxy-3-oxobexanaote (Formula VII).

To a solution of THF (50 mL) and diisopropylamine (37.6 ml), n-Butyl lithium (186.5 ml) at a temperature of –10° C. and maintained at –3° C. for 30 min. To this solution at –20 to –25° C. tertiary butyl acetate (34.97 ml) in 35 ml of THF was added and the temperature was maintianed for 1 h. The ether (14 g) in 14 ml of THF from the above example was added at –20 to –25° C. and maintained for 3 h. The contents were quenched with 3N HCl to a pH of 6–7. The organic layer was separated and the aqueous layer was extracted with EtOAc. The combined organic layer was washed with water, brine, dried and concentrated under reduced pressure to give the title compound of formula VII.

EXAMPLE 1.6
Preparation of tert-butyl 6-cyano-3,5-dihydroxyhexanaote (Formula VIII).

The crude product from the above example was taken up in dry THF and isopropanol under nitrogen atmosphere. The solution was cooled to –10° C. and a solution of zinc borohydride was added. The temperature was maintained between –10° C. to –15° C. and was allowed to warm to room temperature and stand for 18 h. The reaction was quenched by addition of acetic acid and concentrated under reduced pressure to afford an oily residue.

EXAMPLE 1.7
Preparation of (4R)-tert-butyl 6-cyano 3,5-dihydroxy phenylboronato hexanaote (Formula IX).

To the diol from the above example (10 g) was reacted with phenyl boronic acid (5.5 g) in toluene. The contents were refluxed for 20 h and the water was collected by azeotrope distillation. Toluene was removed under reduced pressure and petroleum ether was added to the oily residue was cooled to 0° C. to precipitate the solid boronate.

EXAMPLE 1.8
Preparation of (4R)-tert-butyl 7-amino-3,5-dihydroxy phenylboronato heptanoate (Formula X)

The boronate ester (5 g) from the above example was added to saturated solution of methanolic ammonia and Raney Nickel (5 g) was added. The contents were hydrogenated under pressure (5 kg). The contents were filtered over Celite bed, methanol was removed under reduced pressure to afford the crude title compound of formula X.

EXAMPLE 1.9
Preparation of [R-(R*,R*)]-2-(4-fluorophenyl)-β,δdihydroxy-5-(1-methylethyl)-3-phenyl-4-[phenylaminocarbonyl]-1H-pyrrole-1-heptanoic acid, hemi calcium salt (Formula XII)

A solution of (4R)-tert-butyl 7-amino-3,5-dihydroxy phenylboronato heptanoate (Formula X) and 4-fluoro-α-[2-methyl-1-oxopropyl]γ-oxo-N-β-diphenylbenzenebutane amide (formula IV) and acetic acid in xylene were heated to reflux to 44 h. The solution was diluted with diisopropyl ether and methanol and was washed with dilute methanolic sodium hydroxide solution, dilute HCl and the solvent was then removed under vacuum. The crude oil was stirred with moist silica in $CH_2Cl_2$ and was stirred at room temperature for 18 h. A solution of aqueous NaOH was then added at room temperature and was stirred for 4 h. The reaction mixture was diluted with water and was washed with diisopropyl ether. The aqueous layer was acidified with HCl and was taken up in diisopropyl ether. The crude acid intermediate was then taken up in EtOAc and $NH_3$ gas was bubbled. The contents were stirred for completion of the reaction and solvent was removed upon which the product crystallized. The crude ammonium salt is then taken up in diisopropyl ether-isopropanol mixture and a solution of calcium acetate was added at room temperature upon which the calcium salt precipitated from the solution. The product was filtered and dried under vacuum to get formula XII of acceptable pharmaceutical purity.

The invention has been described by reference to specific embodiments, this was for the purpose of illustration only. Numerous alternative embodiments will be apparent to those skilled in the art and are considered within the scope of the following claims.

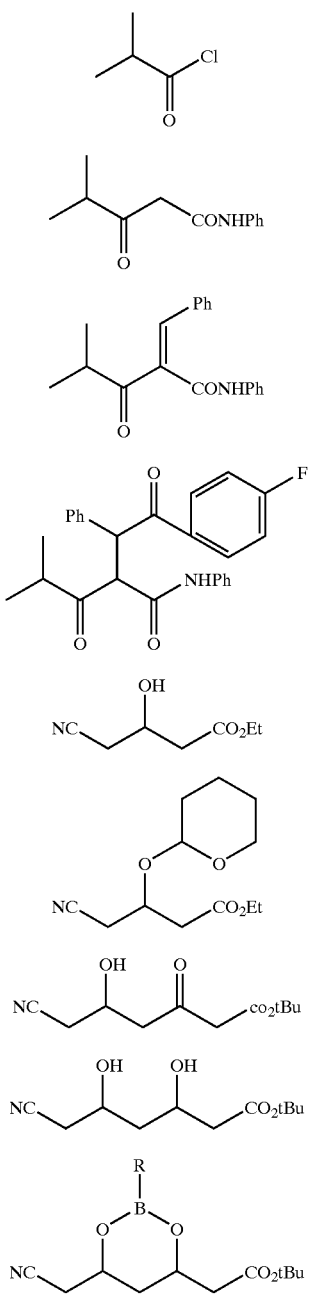

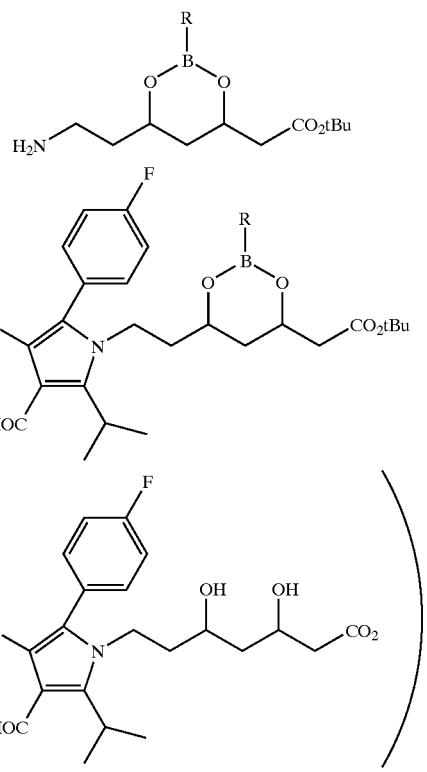

We claim:

1. A process for the synthesis of Atorvastatin of formula XII:

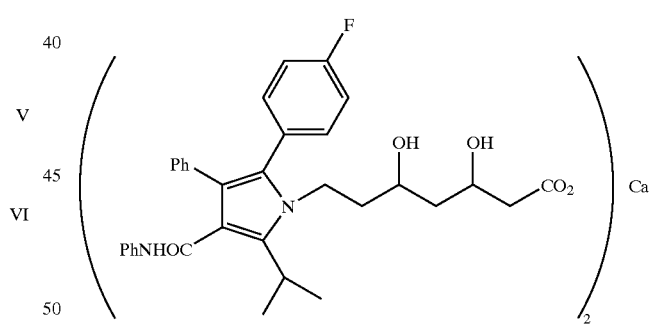

said process comprising steps of:

a) reacting a compound of formula X:

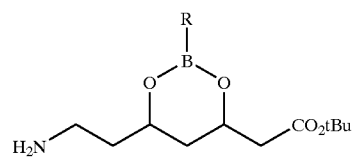

wherein R is selected from $C_6H_5$ or substituted phenyls;

with a compound of structure IV:

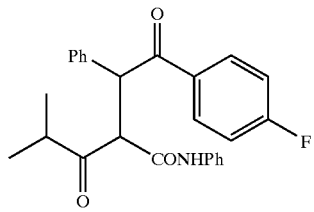

in a mixture of solvents selected from xylene, cyclohexane, methyl tert-butyl ether, diisopropyl ether, and acetonitrile, in the presence of a catalyst selected from pivalic acid, trifluromethyl sulfonic acid, methane sulfonic acid and p-toluene sulfonic acid, to give an intermediate of structure XI:

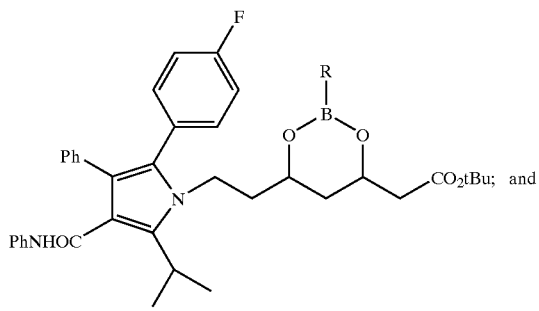

b) hydrolysis of the compound of structure XI followed by calcium salt formation, to get the compound of formula XII.

2. The process of claim 1 wherein the compound of Formula X used in step (a) prepared by:

a) reacting a compound of formula V:

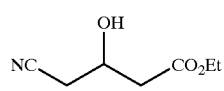

with dihydro pyran to give a protected ether of formula VI:

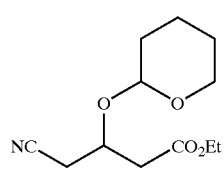

b) reacting the compound of formula VI with tert-butyl acetate with a base at −30 to −80° C. to give a compound off formula VII:

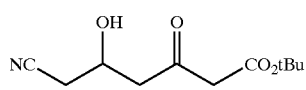

c) reducing a the compound of formula VII with a reducing agent to give a compound of formula VIII:

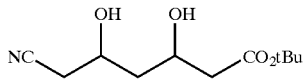

d) reacting the compound of formula VIII with a protecting group to form a protected boronate ester of formula IX:

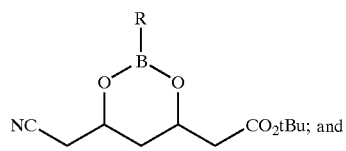

e) reducing the compound of formula IX to give a compound of formula X.

3. The process of claim 2, wherein the reducing agent used in step (c) zinc borohydride.

4. The process of claim 2, wherein the protecting group used in step (d) is selected from phenyl boronic acid, tolyl boronic acid and 3-nitro benzene boronic acid.

5. An intermediate of formula IX:

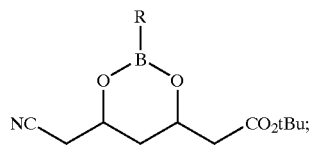

where R is selected from $C_6H_5$ or substituted phenyls.

6. An intermediate of formula X:

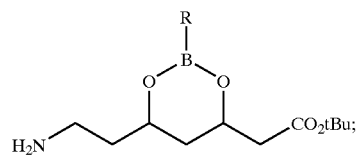

where R is selected from $C_6H_5$ or substituted phenyls.

7. An intermediate of formula XI:

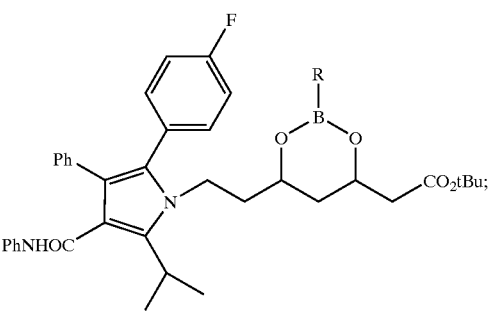

where R is selected from $C_6H_5$ or substituted phenyls.

* * * * *

UNITED STATES PATENT AND TRADEMARK OFFICE
CERTIFICATE OF CORRECTION

PATENT NO.     : 6,867,306 B2                                                              Page 1 of 1
DATED          : March 15, 2005
INVENTOR(S)    : Srinath et al.

It is certified that error appears in the above-identified patent and that said Letters Patent is hereby corrected as shown below:

<u>Title page, Item [54] and Column 1, lines 1-4,</u>
Please replace "PROCESS FOR THE SYNTHESIS OF ATORVASTATIN FORM V AND PHENYLBORONATES AS INTERMEDIATE COMPOUNDS" with -- PROCESS FOR THE SYNTHESIS OF ATORVASTATIN AND PHENYLBORONATES AS INTERMEDIATE COMPOUNDS --

Signed and Sealed this

Seventh Day of June, 2005

JON W. DUDAS
*Director of the United States Patent and Trademark Office*